United States Patent

Eisen et al.

[11] Patent Number: 5,611,849
[45] Date of Patent: Mar. 18, 1997

[54] STABILIZED MONOBUTYLTIN TRICHLORIDE

[75] Inventors: Heinz-Gunther Eisen, Essen; Maria Mecking, Bottrop; Sven-Uwe Vallerien, Essen, all of Germany

[73] Assignee: Th. Goldschmidt AG, Essen, Germany

[21] Appl. No.: 679,283

[22] Filed: Jul. 12, 1996

[30] Foreign Application Priority Data

Jul. 18, 1995 [DE] Germany .................. 195 26 100.3

[51] Int. Cl.$^6$ ................................. C09D 7/12
[52] U.S. Cl. ................................. 106/287.19
[58] Field of Search ........................... 106/287.19

[56] References Cited

U.S. PATENT DOCUMENTS

| | | | |
|---|---|---|---|
| 4,130,673 | 12/1978 | Larkin | 427/255 |
| 4,144,362 | 3/1979 | Larkin | 427/226 |
| 4,530,857 | 7/1985 | Lindner | 427/314 |
| 4,590,096 | 5/1986 | Lindner | 427/109 |
| 4,731,256 | 3/1988 | Russo et al. | 427/109 |

FOREIGN PATENT DOCUMENTS

| | | | |
|---|---|---|---|
| 0132024 | 1/1985 | European Pat. Off. | C03C 17/25 |
| 2541710 | 4/1976 | Germany | C03C 17/23 |

OTHER PUBLICATIONS

Eisen et al, CA 125:167347 "Stabilized monobutyltin trichloride" 1996.

*Primary Examiner*—David Brunsman
*Attorney, Agent, or Firm*—Scully, Scott, Murphy & Presser

[57] ABSTRACT

The invention relates to monobutyltin trichloride which, as a stabilizer, comprises one or more glycerol esters of optionally unsaturated aliphatic carboxylic acids having 1 to 18 carbon atoms.

4 Claims, No Drawings

STABILIZED MONOBUTYLTIN TRICHLORIDE

FIELD OF THE INVENTION

The invention relates to a monobutyltin trichloride (MBTC) which is particularly suitable for hollowware coating and which is stabilized against the influence of moisture and darkening.

BACKGROUND OF THE INVENTION

It is known to apply coatings of all sorts of metal oxides, in particular of tin dioxide, to glass containers in order to improve their resistance to impact and abrasion. This tin dioxide coating acts as a primer for the so-called cold end coating applied after the annealing process.

Customarily, tin compounds are brought into contact with the hot glass surface in vapor or spray form in the so called hot end coating, a thin tin dioxide coating being produced pyrolytically. On account of their physical properties, such as water solubility, vaporizability and the like, and of their low toxicity, monoorganotin trichlorides are, in particular, employed for this purpose (DE-C-25 41 710).

Depending on the purity and quality of the products, however, it has been shown in the processing of these compounds that due to the occurrence of solid particles, in particular after long storage, significant trouble can occur with the glass coating process. significant trouble can occur with the glass coating process.

According to EP-A-0 132 024, to avoid the occurrence of solid particles, dopants of all sorts of types, in particular alcohols, are added to the monoalkyltin trihalides.

A further problem which occurs with monobutyltin trichloride after long storage is darkening, which can lead at its most pronounced to a dark brown coloration. This dark coloration of the product can likewise significantly adversely affect the working process, in particular in measuring and metering operations. Furthermore, with monobutyltin trichloride visible crystallizations very rapidly occur under the influence of moisture; on longer action, presumably caused by hydrate formation, the formation of a liquid multiphase system can even occur.

BRIEF SUMMARY OF THE INVENTION

It has been found that a monobutyltin trichloride composition stabilized against the effects of moisture and darkening is obtained when one or more glycerol esters of aliphatic carboxylic acids are added to it. Suitable esters are the glycerol mono-, di- and triesters of aliphatic, optionally unsaturated carboxylic acids having 1 to 18 carbon atoms. Suitable glycerol esters are, for example, acetates, propionates, 2-ethylhexanoates, valerates, caprylates, dodecanoates and octadecanoates. Particularly active here are glycerol mono- and diacetates or mixtures of the two, and 2-ethylhexanoic acid esters.

Amounts of additive from 0.5 to 10% by weight can be employed; as a rule 0.5 to 1.5% by weight is adequate.

DETAILED DESCRIPTION OF THE INVENTION

The stabilizers employed according to the invention are in this case surprisingly considerably more active than the dopants of the prior art. Thus, for example (see examples), when using 1% glycerol monoacetate crystallization only occurs to 15%, while in the case of the dopants according to EP-A-0 132 024 crystallization is present on the entire surface after the same time.

The activity of the stabilizers employed is explained in greater detail by means of the following examples.
Testing of MBTC for stability to environmental moisture In order to test the effects of environmental moisture on MBTC, MBTC samples standing open are observed and the time is determined after which noticeable changes in the product can be recorded in each case.

For this purpose, clock glasses of 10 cm diameter are provided with 2 ml each of MBTC sample and are exposed next to one another to the surrounding air while standing open in a hood.

The hood front flap is kept open 15 cm above the bottom; the center of the sample glasses is located at a distance of 10 cm from the opening.

The tests are repeated using different positions of the clock glasses relative to one another and the test results meaned in order to compensate for any possible test scatter.

In the experimental arrangement, this crystallization begins at the edge of the liquid surface and then continues inwards.

The table indicates the proportion of the surface crystallized relative to the total surface area. The lower the proportion of the surface crystallized, the better the stabilizing action.

| | | | | | | | |
|---|---|---|---|---|---|---|---|
| Glmono: | glycerol monoacetate | | | | | | |
| Gldiac: | glycerol diacetate | | | | | | |
| Gltriac: | glycerol triacetate | | | | | | |
| Gl-2eth-mono | glycerol 2-ethylhexanoic acid monoester | | | | | | |
| Gl-2eth-di: | glycerol 2-ethylhexanoic acid diester | | | | | | |
| Test period (Hours) | MBTC without additions | MBTC + 1% Ethanol * | MBTC + 0.5% Glmono | MBTC + 1% Glmono | MBTC + 1.5% Glmono | MBTC + 0.5% Gldiac | MBTC + 1% Gldiac | MBTC + 1.5% Gldiac |
| 1 | 100% | 15% | 10% | 5% | 2% | 10% | 5% | 1% |
| 2 | — | 50% | 15% | 10% | 5% | 15% | 10% | 5% |
| 3 | — | 100% | 50% | 15% | 10% | 40% | 15% | 10% |

* Comparison experiment

| Test period (hours) | MBTC + 0.5% Gltriac | MBTC + 1% Gltriac | MBTC + 1.5% Gltriac | MBTC + 1% Gl-2eth-mono | MBTC + 1% Gl-2eth-di |
| --- | --- | --- | --- | --- | --- |
| 1 | 15% | 10% | 5% | 5% | 5% |
| 2 | 20% | 15% | 10% | 5% | 5% |
| 3 | 50% | 25% | 15% | 10% | 10% |

Testing of MBTC for stability to darkening

MBTC darkens on standing in the light, which leads to the initially almost water-clear liquid assuming a dark-brown appearance after some time.

An additional effect which is seen, in particular with the mono/diesters of glycerol, is a stabilization against this darkening, so that this process is considerably slowed.

|  | Starting color | Stored 1 week | Stored 1 month | Stored 3 months |
| --- | --- | --- | --- | --- |
| MBTC + 1% Ethanol | almost water-clear | yellow | light brown | dark brown |
| MBTC + 1% Glmono | almost water-clear | almost water-clear | almost water-clear | light yellow |
| MBTC + 1% Gldiac | almost water-clear | almost water-clear | almost water-clear | light yellow |

\* Comparison experiment

What is claimed is:

1. A composition of monobutyltin trichloride, stabilized against crystallization and against darkening, comprising monobutyltin trichloride and an effective amount of a stabilizer selected from the group consisting of glycerol esters of optionally unsaturated aliphatic carboxylic acids having 1 to 18 carbon atoms, and mixtures thereof.

2. A stabilized composition of monobutyltin trichloride according to claim 1, characterized in that the stabilizer is present in an amount from 0.5 to 10% by weight of the composition.

3. A stabilized composition of monobutyltin trichloride according to claim 1 wherein the stabilizer is glycerol monoacetate, glycerol diacetate or a mixture of both.

4. A stabilized composition of monobutyltin trichloride according to claim 2 wherein the stabilizer is glycerol monoacetate, glycerol diacetate or a mixture of both.

\* \* \* \* \*